US006902904B2

(12) United States Patent
Cutsforth et al.

(10) Patent No.: US 6,902,904 B2
(45) Date of Patent: Jun. 7, 2005

(54) COAGULATION ASSAY REAGENTS CONTAINING LANTHANIDES

(75) Inventors: Gwyn A. Cutsforth, Chapel Hill, NC (US); Donald E. Mahan, Raleigh, NC (US)

(73) Assignee: Pharmanetics Incorporated, Morrisville, NC (US)

( * ) Notice: Subject to any disclaimer, the term of this patent is extended or adjusted under 35 U.S.C. 154(b) by 308 days.

(21) Appl. No.: 09/938,728

(22) Filed: Aug. 27, 2001

(65) Prior Publication Data

US 2003/0044871 A1 Mar. 6, 2003

(51) Int. Cl.$^7$ ................................................. C12Q 1/56
(52) U.S. Cl. ..................................................... 435/13
(58) Field of Search ............................ 435/13; 422/58, 422/61, 7, 73; 436/82, 172

(56) References Cited

U.S. PATENT DOCUMENTS

| | | | | |
|---|---|---|---|---|
| 4,849,340 A | | 7/1989 | Oberhardt | |
| 5,001,069 A | * | 3/1991 | Bartl et al. | 436/86 |
| 5,110,727 A | | 5/1992 | Oberhardt | |
| 5,350,676 A | * | 9/1994 | Oberhardt et al. | 435/13 |
| 5,552,296 A | * | 9/1996 | Adema et al. | 435/13 |
| 5,601,991 A | | 2/1997 | Oberhardt | |
| 5,658,723 A | | 8/1997 | Oberhardt | |
| 5,670,329 A | * | 9/1997 | Oberhardt | 435/13 |
| 5,677,133 A | | 10/1997 | Oberhardt | |
| 6,030,840 A | * | 2/2000 | Mullinax et al. | 436/82 |
| 6,136,271 A | * | 10/2000 | Lorincz et al. | 422/73 |
| 6,245,573 B1 | * | 6/2001 | Spillert | 436/69 |
| 6,395,501 B1 | * | 5/2002 | Rosen et al. | 435/13 |
| 6,482,653 B1 | * | 11/2002 | Kraus et al. | 436/69 |
| 2002/0132370 A1 | * | 9/2002 | Lassen et al. | 436/512 |
| 2003/0027235 A1 | * | 2/2003 | Kraus et al. | 435/13 |

FOREIGN PATENT DOCUMENTS

| | | | |
|---|---|---|---|
| FR | 2689640 | * | 10/1993 |
| WO | WO 98/39654 | * | 11/1998 |

OTHER PUBLICATIONS

Blinc A. Flow Through Clots Determines the Rate and Pattern of Fibrinolysis. Thrombosis and Haemostasis 71(2)230–235, 1994.*
A. Broekmans, et al., "Congenital Protein C Defifciency and Venous Thromboembolism, A Study of Three Dutch Families", The New England Journal of Medicine, vol. 309, No. 6, pp. 340–344, 1983.
J. Griffin, et al., "Protein C, an Antithrombotic Protein, Is Reduced in Hospitalized Patients with Intravascular Coagulation", BIOOD, vol. 60, No. 1 (Jul.), pp. 261–264, 1982.
R. Marlar, et al., "Serial Studies of Protein C and Its Plasma Inhibitor in Patients with Disseminated Intravascular Coagulation", BLOOD, vol. 66, No. 1 (Jul.), pp. 59–63. 1985.

"Protein C in the Treatment of coagulopathy in meningococcal disease", The Lancet, vol. 347, p. 1767, Jun. 1996.
O. P. Smith, et al., "Use of protein–C concentrate, heparin, and haemodiafiltration in meningococcus–induced purpura fulminans", The Lancet, vol. 350, pp. 1590–1593, Nov. 1997.
R. Favier, et al., "Simultaneous administration of antithrombin III and protein C concentrates for the treatment of a devastating coagulopathy in a child", Hematol. Cell Ther., vol. 40, pp. 67–70, 1998.
J. Parkinson, et al., "Stable Expression of a Secretable Deletion Mutant of Recombinant Human Thrombomodulin in Mammalian Cells", The Journal of Biological Chemistry, vol. 265, No. 21, pp. 12602–12610, Jul. 1990.
B. Gerlitz, et al., "Identification of the predominant glycosaminoglycan–attachment site in soluble recombinant human thrombomodulin: potential regulation of functionality by glycosyltransferase competition for serine$^{474}$", Biochem J., vol. 295, pp. 131–140, 1993.
D. T. Berg, et al., "High–Level Expression of Secreted Protein s form Cells Adapted to Serum–Free Suspension Culture", BIOTECHNIQUES, vol. 14, No. 6, pp. 972–978, 1993.
J. Parkinson, et al., "Structure–Function Studies of the Epidermal Growth Factor Domains of Human Thrombomodulin", Biochemical and Biophysical Research Communications, vol. 185, No. 2, pp. 567–576, 1992.
C. E. White, et al., "Large–scale expression, purification and characterization of small fragments of thrombomodulin: the roles of the sixth domain and of methionine 388", Protein Engineering, vol. 8, No. 11, pp. 1177–1187, 1995.
D. E. Jackson, et al., "Purification and characterization of two forms of soluble thrombomodulin from human urine", Eur. J. Biochem., vol. 221, pp. 1079–1087, 1994.
S. M. Richards, et al., "Quantitative and Functional Assays compared for Determination of Zymogen and Activated Human Protein C", Clin. Chem. vol. 36, No. 11, pp. 1892–1896, 1990.
L. Bajzar, et al. "Both Cellular And Soluble Forms of Thrombomodulin Inhibit Fibrinolysis by Potentiating The Activation of Thrombin–activable Fibrinolysis Inhibitor", J. Biol. Chem., vol. 273, No. 5, 1998. Abstract Only.
M. F. Hockin, et al., "Inactivation on human umbilical vein endothelial cells", Arterioscler., Thromb., Vasc. Biol., vol. 17, No. 11, 1997. Abstract Only.

(Continued)

*Primary Examiner*—Ralph Gitomer
(74) *Attorney, Agent, or Firm*—Oblon, Spivak, McClelland, Maier & Neustadt, P.C.

(57) ABSTRACT

A method, kit, system and reagent for performing coagulation assays with higher sensitivity and greater dynamic range is provided which involves the use of one or more metal compounds that interact with calcium binding sites in the blood coagulation cascade, particularly lanthanide compounds, manganese compounds and magnesium compounds. A Protein C reagent, kit, and assay method is also provided using the same type of metal compounds to provide greater detection sensitivity and dynamic range between samples.

23 Claims, 9 Drawing Sheets

OTHER PUBLICATIONS

A. J. Gale, et al., "Nonenzymic anticoagulant activity of the mutant seine protease Ser360Ala–activated protein C mediated by factor Va", Protein Science, vol. 6, No. 1, 1997. Abstract Only.

S. Yu, et al., "Construction, Expression, and Properties of a Recombinant chimeric Human Protein C with Replacementof Its Growth Factor–like Domains by those of Human Coagulation Factor IX", BIOCHEMISTRY, vol. 33, No. 3, 1994. Abstract Only.

C. L. Orthner, et al., "A sensitive and facile assay for the measurement of activated protein C activity levels in vivo", Thromb. Haemostasis, vol. 69, No. 5, 1993. Abstract Only.

K. G. Mann, et al., "Active site–specific immunoassays", BLOOD, vol. 76, No. 4, 1990. Abstract Only.

K. F. Stocker, et al., "Snake protein C activator, methods of preparation and use thereof", US Patent. Abstract Only.

S. Nakamura, et al., "Assay methods for protein C (and protein S)", Rinsho Byori, Rinji Zokan, vol. 70, 1987, Abstract Only.

G. A. Soff, et al., "Protein C levels in nephrotic syndrome: use of a new enzyme–linked immunoadsorbent assay for protein C antigen", Am. J. Hematol., vol. 22, No. 1, 1986. Abstract Only.

R. M. Bertina, et al., "The use of a functional and immunologic assay for plasma protein C in the study of the heterogeneity of congenital protein C deficiency", Throb. Haemostasis, vol. 51, No. 1, 1984. Abstract Only.

A. Blinc, et al., Flow Through Clots Determines the Rate and Pattern of Fibrinolysis. Thrombosis and Haemostasis, 1994, vol. 71, No. 2, pp. 230–235.

Written Opinion, PCT/US02/03357, International filing date: Feb. 7, 2002, 4 pages.

* cited by examiner

COAGULATION ASSAY REAGENTS CONTAINING LANTHANIDES

BACKGROUND OF THE INVENTION

1. Field of Invention

The present invention relates to improved coagulation assay reagents containing lanthanide compounds, and the assays performed therewith, particularly a protein C assay using a lanthanide containing reagent having surprising improvements in sensitivity of the assay.

2. Discussion of the Background

In this document, the term "coagulation assay" is used to denote a class of assays which includes (i) clotting or clot formation assays, (ii) clot lysis assays, and (iii) clotting parameter(s) assays.

Blood clotting reactions, in general, employed as clinical assays measure the time required for the formation of a fibrin clot. The most common of these reactions is the prothrombin time test.

Many approaches exist for measuring clot formation in prothrombin time assays. All of these clot formation based assays utilize thromboplastin to react with the patient's blood sample. Available approaches differ in the means used to detect when clot formation occurs. They may also differ in the types of apparatus used and in the constituents of and/or additives to the reagent.

Blood clotting assays are principally used for screening, diagnosis, and for monitoring patients receiving anticoagulant therapy. There are many types of coagulation assays. These include prothrombin time (PT), partial thromboplastin time (PTT), activated partial thromboplastin time (APTT), fibrinogen assay, thrombin clotting time (TCT), activated clotting time (ACT), etc. The most frequently performed of these assays is prothrombin time.

A principal use of prothrombin time (PT) determinations is to monitor patients receiving oral anticoagulants such as warfarin. An accurate monitoring of coagulation in these patients is important to prevent recurrent clotting (thrombosis) and to keep the coagulation mechanism sufficiently active to prevent spontaneous bleeding. Prothrombin time testing provides information to permit better drug control to be achieved through the regulation of drug dosage.

In conventional practice, PT assays are performed by the addition of a liquid reagent to a plasma sample. The reagents are typically supplied in dried form and consist primarily of tissue thromboplastin and calcium chloride. The dried reagent is reconstituted before use by addition of a measured amount of distilled water.

These reagents are thermally sensitive, and refrigeration prior to use is required. The shelf life of the reagent in dried form is from one to two years. However, when it is reconstituted the reagent is considerably more labile and must be used within a few hours or discarded. In some cases reconstituted reagents can be kept for a few days under refrigeration.

Prothrombin time assays are performed by mixing sample and reagent at 37° C., and monitoring the progress of the reaction until a perceptible clot (or "gel clot") is detected. The development of a gel clot is the end point of the reaction. This end point may be detected in various ways; by viscosity change, by electrode reaction, and, most commonly, by photometric means. The test result is generally compared to a result using a normal (control) plasma.

Before performing the test, a blood sample is collected in a tube or syringe containing anticoagulant (citrate). The blood sample is centrifuged, and the plasma separated (e.g., by decantation) from the red blood cells. A measured quantity (usually 0.1 ml) of plasma is pipetted into the reaction vessel or cuvette. A measured amount of reagent is then added manually via pipette or automatically by means of other volumetric delivery systems capable of metering a known, preset quantity of reagent. Alternatively, the sample can be added to the reagent directly.

Typically, 0.2 ml of reagent is employed. The addition of the reagent initiates the reaction. Many existing blood clotting assays, and in particular PT assays, all suffer from at least one of the following disadvantages: difficulty in performance, requirement of highly trained personnel, inaccuracy in measurement, reagent instability, large consumption of reagent, etc.

One solution to this problem was addressed in Oberhardt, U.S. Pat. No. 5,110,727, in which a dry reagent based reaction slide is provided for performing coagulation assays quickly, accurately and simply. Such tests are marketed by Pharmanetics, Inc.

The capacity of blood to clot, as well as to not clot, is dependent on a large number of factors and cofactors. The ability of central clinical laboratories to reliably and conveniently assay for Protein C in whole blood or plasma samples can be critical in monitoring individuals for whom an inappropriate coagulation episode is a life-threatening problem. The blood coagulation system is dominated by sequential proteolytic activation reactions of inactive precursors, called zymogens. Forward clotting reactions are controlled by simultaneous activation of anticoagulant zymogens that serve to limit the extent of clot formation and initiate the fibrinolytic system to resolve the clot. A crucial enzyme in the cascade is thrombin. Thrombin proteolyzes fibrinogen to form a clot from insoluble fibrin molecules. Thrombin is a poor activator of Protein C in solution. At the same point in the coagulation cascade, thrombin may bind to thrombomodulin on the endothelial cell surface and become a potent activator of Protein C but no longer have the ability to cleave fibrinogen to fibrin. Generation of low levels of thrombin favors binding to thrombomodulin and activation of Protein C. Activated Protein C proteolytically inactivates Factors Va and VIIIa to reduce the rate of thrombin formation.

Decreased levels and/or activity of Protein C is associated with an increased thrombotic risk. The thrombotic risk may present itself as a deep venous thrombosis or as disseminated intravascular coagulation (DIC). Broekmans, A. W. et al, *N. Engl. J. Med.*, 309, 340–344 (1983). The concentration of Protein C has been correlated to these thrombotic events and to the severity of the event. Griffin J. H. et al, *Blood*, 60(1), 261–264 (1982); Marlar R. A. et al, *Blood*, 66(1), 59–63, (1985). There have been several reported uses of Protein C concentrates, purified Protein C and activated Protein C to treat and prevent DIC. Rintala E. et al, *Lancet*, 347, 1767 (1996); Smith, O. P. et al, *Lancet*, 350, 1590–1591 (1997); Favier R. et al, *Hemat. Cell Ther.*, 40, 67–70 (1998).

FDA 510(k) approved Protein C assays can be broadly grouped into three categories: antigenic, chromogenic/amidolytic, and coagulometric. The antigenic assays include ELISA, EIA and RIA type tests. These assays do not determine if the protein is functional because the antibodies are not directed to epitopes associated with functional activity.

The chromogenic/amidolytic assays rely on the ability of the active site of the enzyme to cleave a small synthetic substrate to release an intensely colored product. There may exist a discrepancy between the activity of activated Protein C towards a synthetic substrate and towards a natural biological substrate. In addition, other functional characteristics of the enzyme (i.e. cofactor interaction) are not tested by the synthetic substrate.

Coagulometric assays performed in the central laboratory are cumbersome and are best suited to batch analysis. These assays require generation of a standard curve prior to sample analysis. The samples require an initial dilution, an incubation for activation of the Protein C, then initiation of the clotting cascade. The relationship between clot time and Protein C activity (expressed as percent of normal) established by the standard curve is used to interpolate the Protein C activity of the unknown sample. Although differences in laboratory procedure exist, a standard curve is routinely repeated with each group of patient samples tested, when new lots of reagent are opened or when the control does not fall within its prescribed range. The multiple manipulations required for determination of one sample provides an assay that is cumbersome and batch analysis is more economical in terms of technologist time and reagent costs.

There is thus a strongly felt need for a simple, facile and accurate method for the performance of blood clotting assays, e.g., in medical applications. Such a method should be based on a minimum number of manipulations of either a sample or reagent. Ideally such a method should be easily utilized by persons without extensive clinical laboratory training and should require no sample or reagent-containing solution preparation. It should not suffer the problems associated with reagent instability and be very accurate. It should permit effective mixing of sample and reagent. It should require only a very small amount of sample. And it should be able to perform automatic treatments of the sample, e.g., it should not require centrifugation of the blood sample or any other off line cell separation process. Available clotting parameter assays likewise suffer salient disadvantages.

Clotting parameter assays are referred to herein as function and structure-based assays in the broad realm of coagulation diagnostics which do not utilize clot formation or clot lysis processes to generate end points. Most of these assays utilize chromogenic synthetic substrates to quantify molecular markers or specific factors or components associated with coagulation. These are typically functional reaction based assays as opposed to most immunoassays which could detect the same molecules but utilize structure recognition and may therefore still identify inhibited components or defective components, neither of which may be functional. The present invention does not deal specifically with immunoassays but may be generally applicable to homogeneous chromogenic and fluorogenic immunoassays.

SUMMARY OF THE INVENTION

Accordingly, one object of the present invention is to provide an improved coagulation assay having higher sensitivity and greater dynamic detection range.

A further object of the present invention is to provide a clotting parameter control that has clotting time ranges simulating abnormal plasma.

A further object of the present invention is to provide a Protein C coagulation assay of high sensitivity that can be performed in minutes at the bedside.

A further object of the present invention is to provide a Protein C coagulation assay for direct determination of the functional activity of zymogen Protein C.

A further object of the present invention is to provide reagents for coagulation assays that provide the assay with greater dynamic detection range and increased sensitivity.

These and other objects of the present invention have been satisfied by the discovery of assays, reagents, methods and kits for performing coagulation assays which use the addition of one or more metal compounds, preferably lanthanide compounds, manganese compounds, or magnesium compounds, that interact with calcium binding sites in the blood coagulation cascade, and the extension of the use of these metal compounds to provide a Protein C assay having high sensitivity and dynamic detection range.

BRIEF DESCRIPTION OF THE DRAWINGS

Many attendant features of this invention will become readily appreciated as the same becomes better understood by reference to the following detailed description when considered in connection with the accompanying drawings.

DETAILED DESCRIPTION OF THE PREFERRED EMBODIMENTS

The present invention relates to reagents for the performance of coagulation assays that provide increased sensitivity and greater dynamic detection range by the use of one or more added lanthanide metals, preferably as lanthanide compounds, wherein the reagents are suitable for use in coagulation assays such as those described in U.S. Pat. Nos. 4,849,340; 5,110,727; 5,350,676; 5,601,991; 5,658,723; 5,670,329; and 5,677,133, the entire contents of which are hereby incorporated by reference (hereafter referred to as the "Oberhardt patents").

In the present invention, magnetic particles are induced to move by being subjected to either (1) an oscillating magnetic field or (2) a moving permanent magnetic field or (3) a combination of an oscillating magnetic field and a stationary permanent magnetic field, or (4) a rotating magnetic field. The movement of the magnetic particles is then monitored in the performance of the assay.

The magnetic field of the present invention can be generated using any of the magnetic field generating means described in the Oberhardt patents. The movement of the magnetic particles is preferably detected also as described in the Oberhardt patents.

The clotting assays of this invention are performed on a reaction element. This reaction element can be any element which will support the reagents used in the assay and permit monitoring movement of the magnetic particles. Such reaction elements include microtiter plates, their equivalents, substantially flat surfaces or the reaction slide provided by the Oberhardt patents.

The reagents used in the present invention are those used in the assays described herein. They are distinguished, in part, by the fact that they contain, in intimate admixture, magnetic particles. The magnetic particles are present in an amount of 0.5, or lower, to 50 milligrams of magnetic particles, preferably 1 to 10 milligrams, per milliliter of dry reagent.

The clotting assays of the present invention include prothrombin time (PT), partial thromboplastin time (PTT), activated partial thromboplastin time (APTT), thrombin clotting time (TCT), fibrinogen, heparin management test (HMT), protamine response time (PRT), heparin response time (HRT), low molecular weight heparin (LMWH), low range heparin management test (LHMT), and ecarin clotting time (ECT), with the reagents for each of these tests as described in the Oberhardt patents, with the primary difference being in the addition to the reagent of one or more metal compounds that interact with Ca binding sites in the coagulation cascade. Within the context of the present invention, the various assays are given the names above, as described in the various Oberhardt patents. However, the name of the assay is not critical and could change, even though the parameter being measured is still the same.

Any metal containing compound that interacts with calcium (Ca) binding sites in the blood coagulation cascade may be used in the assays of the present invention. Preferably the metal compound is any compound providing a cation of the lanthanide series, as well as compounds providing a cation of manganese or magnesium. More preferably, the metal compound is a compound of magnesium, manganese, terbium, gadolinium, europium, lanthanum. Suitable compounds of these cations should be soluble in the sample to be tested and include salts of organic acids (aliphatic as well as aromatic acids), halides, C2–C6 alkyl esters of organic acids, hexafluorophosphates, nitrates, oxalates, perchlorates, tetrafluoroborates, trifluoromethansulfonates (triflates), substituted and unsubstituted C4–C8 alkanedionates, citrates, acetylacetonates, and sulfates, preferably salts of acetates or benzoates, bromides, chlorides, 2-ethylhexanoates, tris(2,2,6,6-tetramethyl-3,5-heptanedionates, 2,4-pentanedionates, and salicylates, more preferably chlorides and acetates.

Additionally, the addition of one or more metal compounds that interact with calcium binding sites, preferably lanthanide compounds, to control samples for the above assays provide controls having specific clotting time ranges simulating abnormal plasma.

The one or more metal compounds are added to the reagents in an amount of from 2 mM (millimolar) to 10 mM, preferably 2 mM to 7 mM, more preferably 3 mM to 5 mM. Above 10 mM, a loss in sensitivity in the assay is typically observed. In the above noted assays, the addition of the metal compound increases the dynamic range of the assay by providing greater detection differences between samples with low amounts of the particular clotting parameter being measured and high amounts of the clotting parameter being measured.

The present invention also provides a one-stage assay using a Protein C activator for directly determining the functional activity of zymogen Protein C in a format designed for single sample determinations. This embodiment of the present invention is preferably designed to be used in the same reaction element and detection system described above for coagulation assays. This assay uses a reagent comprising an initiator of the intrinsic coagulation pathway or Factor X, a Protein C activator (such as thrombomodulin, Protac®, other catalytic or stoichiometric activators), calcium ions, one or more metal compounds that interact with calcium binding sites in the coagulation cascade, preferably one or more lanthanide compounds, and optionally bulkers and/or stabilizers.

In this embodiment of the present invention, the concentration of Protein C can be correlated to clot time, the rate of clot formation, the integrity of the final clot (i.e. clot strength), or any combination of the three (i.e. integration of the signal from time point A to time point B). The assay can be calibrated to a standard control plasma to establish the relationship between the measured signal and the Protein C concentration. The standard control curve can be generated immediately prior to sample measurement, if desired, or can be a paper or electronically stored standard control curve. No user calibration of the system is required.

The test sample for the Protein C assay of the present invention can be citrated whole blood or plasma. The sample can be used as is or can be diluted in a Protein C depleted plasma, preferably 1 part sample to 5 parts depleted plasma, to reduce the concentration of interfering substances and replenish any coagulation factors that may be depleted due to a genetic or clinical condition. Also, if desired, polybrene or another heparin antagonist can be added to the diluted sample (or alternatively added to the diluent plasma) to prevent interferences from unfractionated heparin and low molecular weight heparins. The amount of polybrene or other heparin antagonist should be sufficient to compensate for the presence of 1 U/ml unfractionated or low molecular weight heparin in a plasma sample at the preferred dilution level of 1 part sample to 5 parts depleted plasma, as noted above. The polybrene or other heparin antagonist, when used, is preferably added in an amount of at least 5 µg/ml (micrograms/milliliter), preferably at least 7 µg/ml, more preferably at least 10 µg/ml, relative to diluted plasma. Suitable other heparin antagonists include, but are not limited to, protamine sulfate and heparinase, although polybrene is most preferred. Use of heparinase provides a preferred effective concentration of 40 U/ml being sufficient to reduce interference from 1 U/ml of unfractionated heparin, without the need for incubation.

In the Protein C assay of the present invention, the sample is added to the reaction chamber containing the Protein C assay reagent. The present Protein C assay reagent comprises a Protein C activator, an initiator of the intrinsic coagulation pathway or of Factor X, calcium ions and one or more lanthanide compounds. The lanthanide compounds useful for the Protein C assay of the present invention include those listed above for the other coagulation assays.

In the Protein C assay, the reaction proceeds with an initial lag time during which it is believed that thrombomodulin is capturing thrombin and activating Protein C. In preferred embodiments of the present Protein C assay, the coagulation of the sample starts after about at least 200 seconds, preferably after about at least 250 seconds, more preferably after about at least 300 seconds. The initial lag time can vary from several seconds to around 5–7 minutes, with the longer lag times being more preferred and providing better dynamic range in the final determination.

Figure 1:
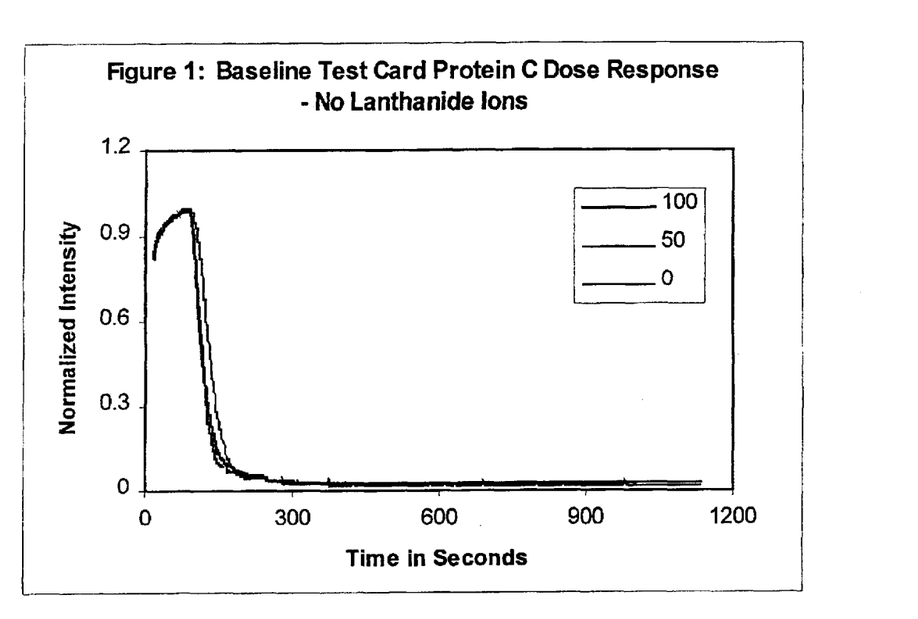
FIG. 1 shows the baseline test card Protein C dose response using the assay method of the present invention, but without the addition of the metal compound that interacts with calcium binding sites in the coagulation cascade.
Figure 2:
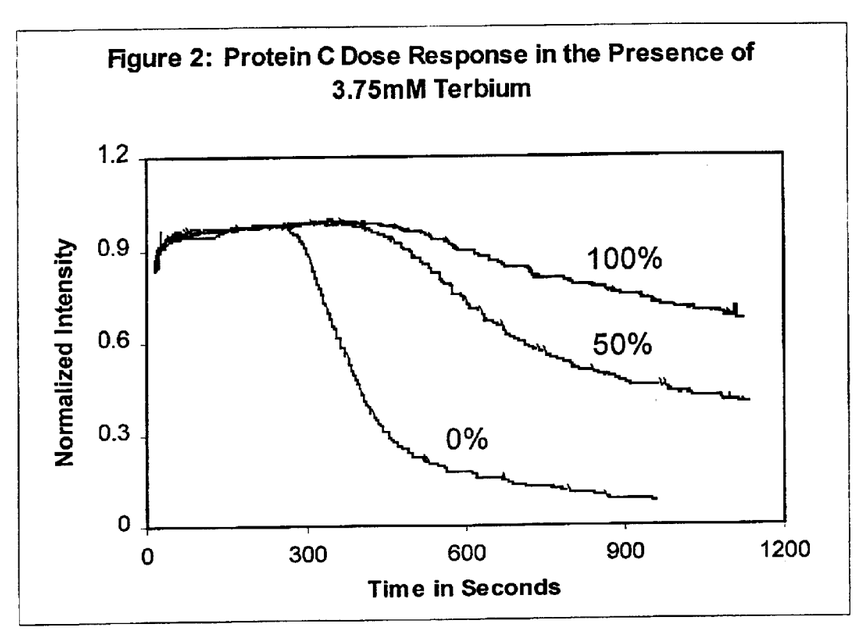
FIG. 2 shows the Protein C dose response using the present assay with added terbium.
Figure 3:
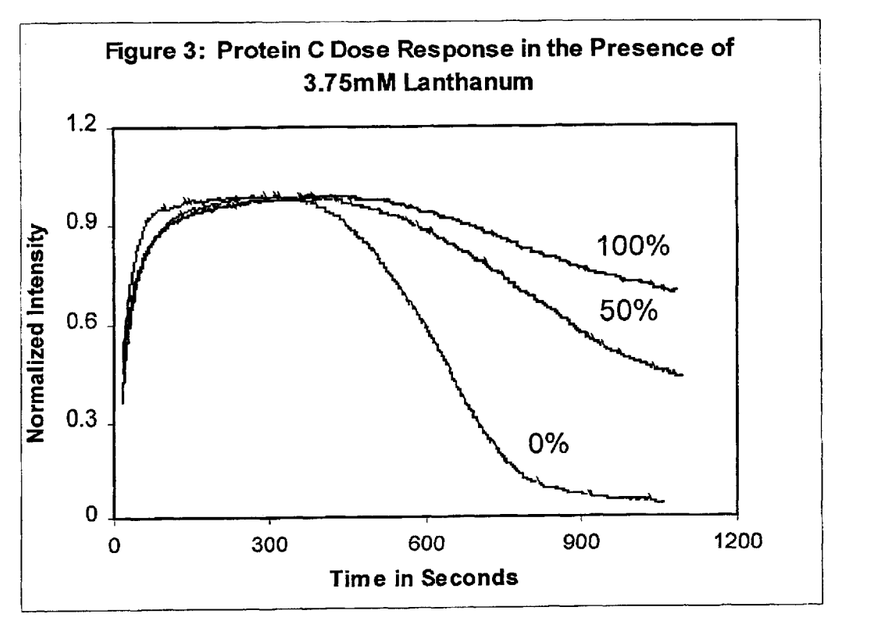
FIG. 3 shows the Protein C dose response using the present assay with added lanthanum.
Figure 4:
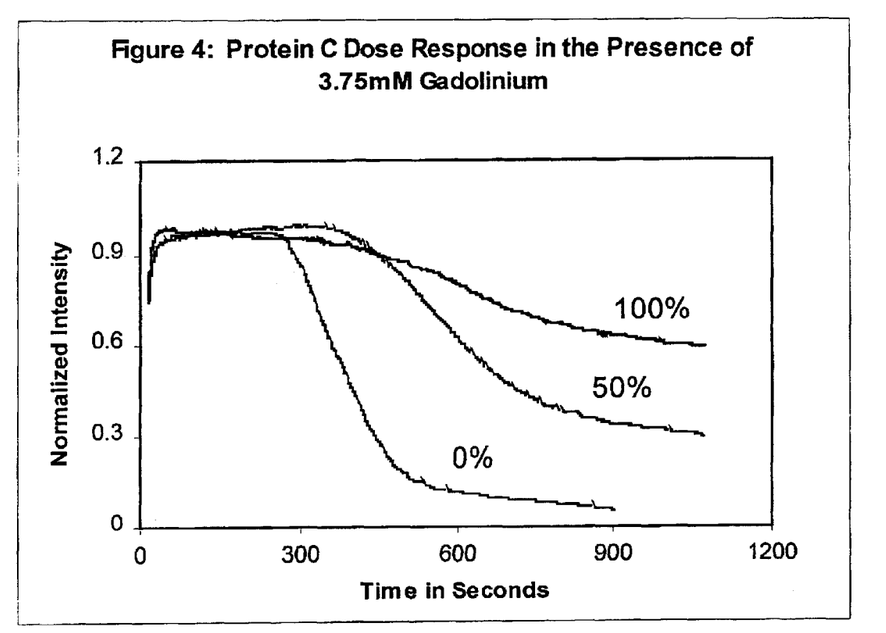
FIG. 4 shows the Protein C dose response using the present assay with added gadolinium.
Figure 5:
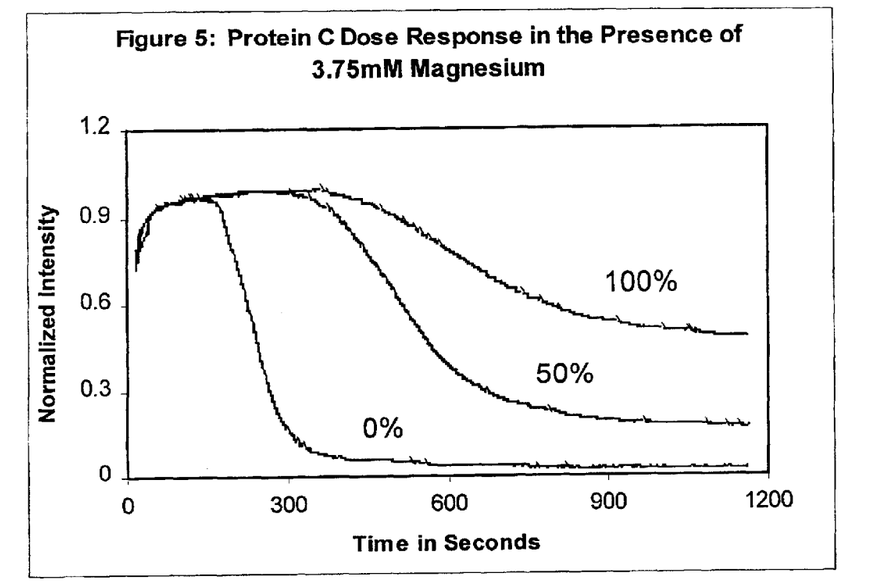
FIG. 5 shows the Protein C dose response using the present assay with added magnesium.
Figure 6:
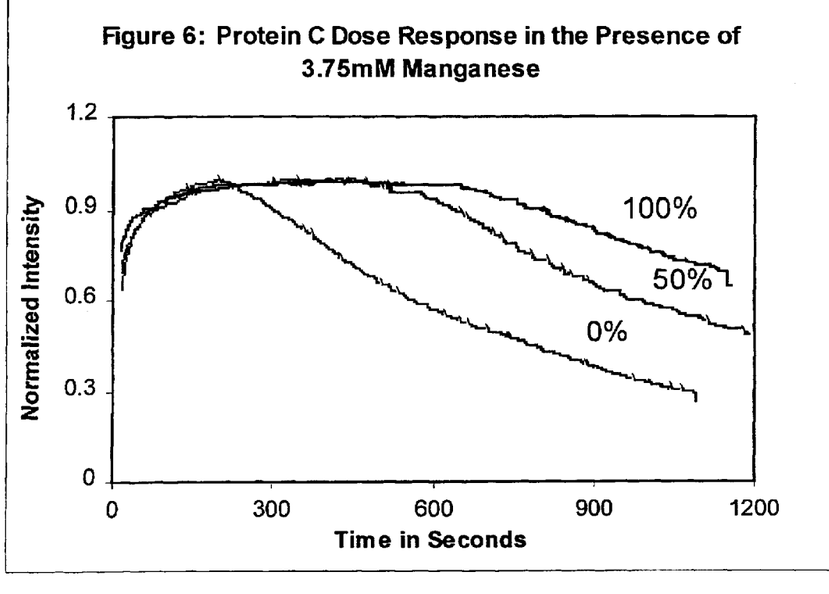
FIG. 6 shows the Protein C dose response using the present assay with added manganese.
Figure 7:
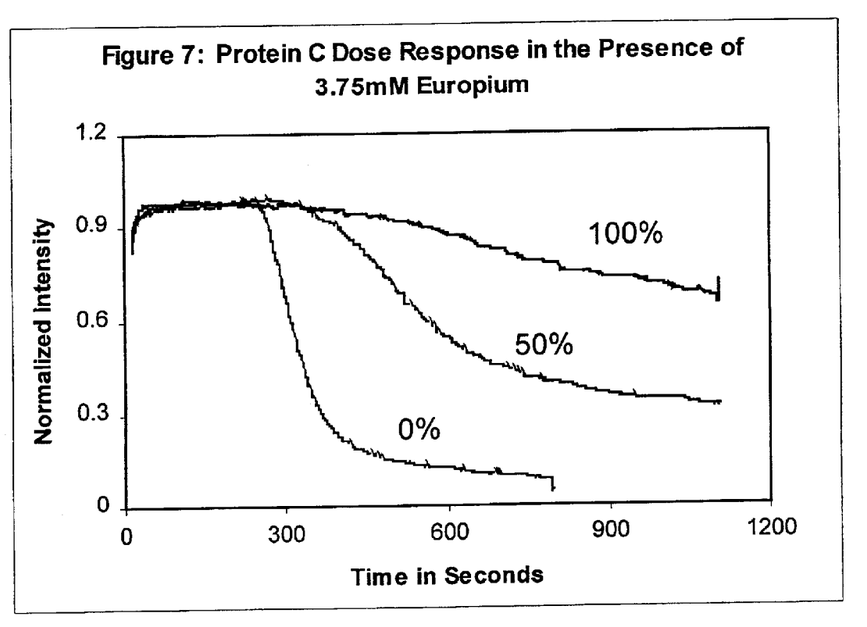
FIG. 7 shows the Protein C dose response using the present assay with added europium.

If the Protein C assay is performed without the metal compound present, the resulting assay curve generated by the present detection system shows little or no difference between samples ranging from 100% Protein C to 0% Protein C. However, the addition of the metal compound of the present invention causes the response curves to separate, providing a dramatic increase in sensitivity, typically on an order of magnitude increase. This separation of the response curves is illustrated by comparing FIGS. 2–7 with FIG. 1. In FIG. 1, the Protein C assay was performed using three samples having 0%, 50% and 100% Protein C, without the presence of a metal compound as required in the present assay. As readily seen in the Figure, the curves show essentially no difference, making it nearly impossible to determine the level of Protein C. However, the addition of the metal compound to the reagent in the assay gives a clear separation of the three sample curves, allowing the assayist to readily obtain a quantitative measurement of the Protein C concentration in the sample. The same three levels of Protein C are readily separately detected with the addition of the metal compound of the present assay. FIGS. 2–7 show the Protein C dose responses upon addition of terbium, lanthanum, gadolinium, magnesium, manganese and europium, respectively.

In the Protein C assay of the present invention, the initiator of the intrinsic coagulation pathway or of Factor X can be any substance capable of triggering the coagulation cascade, such as ThromboScreen® Kontact®, commercially available from Pacific Hemostasis of Huntersville, N.C. Other coagulation initiators of Factor X, prothrombin time (PT), and activated partial thromboplastin time (APTT) can also be used, including reagents reconstituted from purified components.

As Protein C activator, thrombomodulin is preferred, although other activators can be used as described below. The thrombomodulin preferably used in the Protein C assay of the present invention can be natural thrombomodulin or recombinant thrombomodulin. The recombinant thrombomodulin is preferred, particularly recombinant, soluble, human thrombomodulin, as it is essentially free of cytoplasmic and transmembrane domains, as well as the chondroitin sulfate side chains. (See Gerlitz, *Biochem. J.*, 295, 131–140 (1993); *Biotechniques*, 14(6), 972–978 (1993); and Parkinson et al, *Biochem. Biophys. Res. Comm.*, 185(2), 567–576 (1992)). Other commercially available thrombomodulins can also be used, such as thrombomodulins from different tissues and species as well as different recombinant molecules. Additionally, other Protein C activators, such as snake venoms (such as reptilase or ecarin), can be used in the present assay. The amount of Protein C activator should be sufficient to activate Protein C and bring about the onset of coagulation in a time period of at least 1 min or more, preferably at least 2 min or more, more preferably at least 3 min or more. In wet assays (performed in an environment other than the preferred test card dry chemistry format) the amount of Protein C activator is preferably from 3 to 20 pm/test (picomoles/test), more preferably from 5 to 10 pm/test. For the preferred dry chemistry format test card, the amount of Protein C activator is preferably from 20 to 150 pm/test, more preferably from 20–35 pm/test for undiluted samples and more preferably from 50 to 135 pm/test for diluted samples. As examples of thrombomodulins useful as the Protein C activator in the present assay (but not intended to be limiting as to the different types of thrombomodulins that can be used), the following table is provided:

| Thrombomodulin | Wet Testing picomoles/test | Dry card/ Undiluted picomoles/test | Dry card/Diluted picomoles/test |
|---|---|---|---|
| Eli Lilly TMD1 | 5 | 35 | 135 |
| Berlex B240 | 5–10 | 20–30 | <100 |

For most preferred embodiments of the present Protein C assay, the amount of time to initiate clot formation in wet testing is about 200 seconds, with dose response curves being completed in about 600 seconds. For both neat and diluted samples, the initiation of clot formation using the dry chemistry format is approximately 250 seconds, and dose response curves are complete in about 900 seconds.

Examples of this invention are set forth below. However, it is to be understood that these examples are given by way of illustration only and are not to be construed as limiting the invention either in spirit or in scope, as many modifications both in doses and methods could be possible to those skilled in the art.

EXAMPLES

A Protein C test card was prepared using methods as described in Oberhardt patents, but using a reagent formulation as follows:

11–12.5 mM calcium chloride

3–5 mM terbium chloride 0.2 mg/ml BSA (bovine serum albumin)

5–7 wt % PIOP (paramagnetic iron oxide particles)

45% by volume of Kontact® (available from Pacific Hemostasis)

100 g/L of lactose (as cryoprotectant/bulker/stabilizer)

100 g/L of mannitol (as cryoprotectant/bulker/stabilizer)

15 mM HEPES buffer, pH=7.85

125–150 pm/test rhTM (recombinant, human Thrombomodulin available from Eli Lilly Co.)

Test Card Manufacture—Reagent was prepared and used on the same day. The reagent was maintained at 2–8° C. until placed in the water bath of the assembly machine. The assembly machine water bath was maintained at 15° C. Test cards were assembled and immediately flash frozen in liquid nitrogen chambers in test card trays holding approximately 800 test cards per tray. After assembly of all test cards in the 3,300 card lot the trays were placed in a lyophilizer chamber. At the end of the 40 hour lyophilization run the test cards were removed from the trays for packaging. Test cards were 'turned and sorted' for poorly filled test cards before packaging. Cards were packaged with desiccant in heat-sealed foil packaging. Packaged test cards were refrigerated overnight before analysis.

Test Card Analysis

Test cards were removed from the refrigerator and were allowed to come to room temperature for at least 30 minutes. One ml aliquots of Factor Analyzed ConTrol plasma (FACT, George King Biomedical, Overland, Kans.) was removed from the −70° C. freezer and thawed for five minutes in a 37° C. water bath. The plasma was cooled for 10 minutes in a melting ice bucket. Protein C deficient plasma (American Diagnostica, Piscataway, N.J.) was rehydrated according to package insert instructions and pooled. Protein C standards were prepared by mixing appropriate volumes of the two plasmas (FACT and Protein C deficient) to generate seven concentrations of Protein C from 0–100% of normal following the chart below.

| % of normal PC | Vol. FACT | Vol. C def. |
|---|---|---|
| 100% | 200 μl | 0 μl |
| 75% | 150 μl | 50 μl |
| 65% | 130 μl | 70 μl |
| 50% | 100 μl | 100 μl |
| 35% | 70 μl | 130 μl |
| 25% | 50 μl | 150 μl |
| 0% | 0 μl | 200 μl |

The plasmas were mixed by vortexing three times for approximately fifteen seconds at full speed. All plasma samples were kept on ice for the duration of the experiment. TAS™ analyzers were set for 'Real Time' data collection, i.e. collection of the signal intensity every half-second without application of a slope or offset. Testing was initiated on the TAS™ analyzers by swiping the analyzers with a Real Time APTT MasterCard. A Protein C test card was placed into each of thirteen analyzers and warmed to 37° C. Thirty microliters of sample was pipetted into the sample well and the test initiated. The test was allowed to collect data for 1000 seconds before the test card was removed from the TAS™ analyzer chamber. The data was saved and is presented in two forms: average wave forms and average area under the curves.

Average Wave Forms

Figure 8:
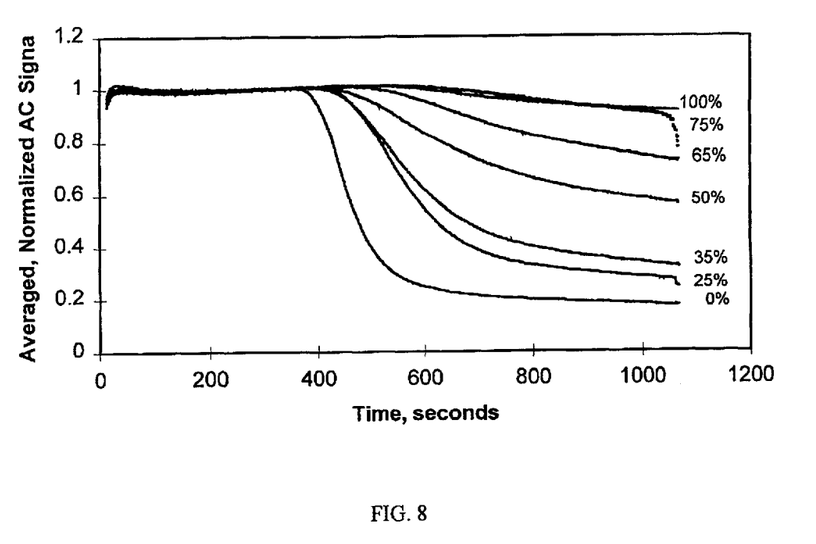
FIG. 8 shows Protein C dose responses for various known levels of Protein C.
Figure 9:
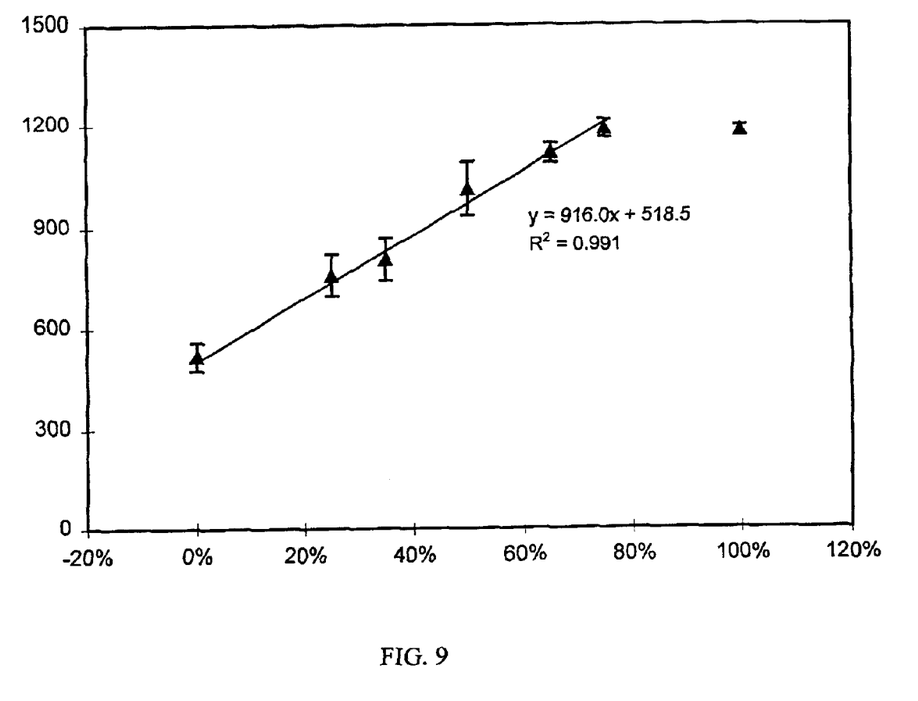
FIG. 9 shows a Protein C standard curve obtained from the area under the curves of FIG. 8.

The thirteen replicates for each of the Protein C standard samples were normalized to the intensity at 300 seconds. Each analyzer and the same sample run repeatedly on the same sample will not generate the same intensity of signal. Therefore, a normalization step is preferred to become intensity independent for quantification of Protein C concentration. The average wave form was calculated for each of the seven Protein C standard samples from the normalized wave forms, and is shown graphically in FIG. 8. The intensity of the individual normalized wave forms were integrated from 300 to 900 seconds (data shown in table below) to generate a Protein C standard curve, shown in FIG. 9. The area under the curve (synonymous with integration) was averaged for each of the Protein C standard samples from the 13 calculated replicate areas. Error bars represent one standard deviation from the mean.

Average Area Under the Curves

| % of normal PC | Average Area | Standard Deviation | C.V. |
| --- | --- | --- | --- |
| 100% | 1182 | 16.0 | 1.4% |
| 75% | 1189 | 26.7 | 2.2% |
| 65% | 1116 | 28.9 | 2.6% |
| 50% | 1015 | 77.7 | 7.7% |
| 35% | 807 | 62.8 | 7.8% |
| 25% | 758 | 62.8 | 8.3% |
| 0% | 516 | 41.7 | 8.1% |

It will be apparent from the above detailed description that there are many variations in the present invention and thee same are deemed to be subject to this invention as set forth in the appended claims.

What is claimed is:

1. A dry coagulation assay reagent comprising magnetic particles distributed substantially homogeneously therethrough wherein said reagent is selected from the group consisting of:
   (1) one member selected from the group consisting of prothrombin time reagents and (ii) prothrombin time reagents and calcium salts;
   (2) partial thromboplastin time reagents with calcium chloride;
   (3) partial thromboplastin time reagents with calcium chloride and clot formation activators;
   (4) thrombin or a snake venom with thrombotic activity;
   (5) fibrin, or plasminogen and fibrin;
   (6) plasminogen activator assay reagents containing (i) plasminogen and (ii) either fibrin, a snake venom with thrombotic activity, or thrombin;
   (7) plasminogen assay reagents containing (i) a plasminogen activator and (ii) either fibrin, a snake venom with thrombotic activity, or thrombin;
   (8) natural and synthetic plasminogen activators;
   (9) alpha-2-antiplasmin assay reagents containing fibrin and plasmin; and
   (10) combinations thereof,
wherein the reagent further comprises one or more lanthanide metal compounds that interact with calcium binding sites in a blood coagulation cascade.

2. The reagent of claim 1, wherein said one or more lanthanide metal compounds are selected from the group consisting of compounds of europium, lanthanum, gadolinium and terbium.

3. The reagent of claim 1, wherein said one or more lanthanide metal compounds are selected from the group consisting of salts of organic acids, halides, C2–C6 alkyl esters of organic acids, hexafluorophosphates, nitrates, oxalates, perchlorates, tetrafluoroborates, trifluoromethanesulfonates, substituted and unsubstituted C4–C8 alkanedionates, acetylacetonates, and sulfates.

4. The reagent of claim 1, wherein said reagent is thromboplastin or thromboplastin and a calcium salt.

5. The reagent of claim 1, wherein said reagent is a partial thromboplastin time reagent with calcium chloride.

6. The reagent of claim 1, wherein said reagent is a partial thromboplastin reagent with calcium chloride and a clot formation activator.

7. The reagent of claim 1, wherein said reagent is thrombin or a snake venom with thrombotic activity.

8. The reagent of claim 1, wherein said reagent is fibrin, plasminogen and fibrin, a snake venom with thrombin-like activity, or thrombin.

9. The reagent of claim 8, comprising either said snake venom with thrombotic activity or a combination of said snake venom with thrombotic activity and thrombin.

10. The reagent of claim 1, wherein said reagent is a plasminogen assay reagent containing (i) a plasminogen activator and (ii) either fibrin, a snake venom with thrombotic activity, or thrombin.

11. The reagent of claim 10, comprising either said snake venom with thrombotic activity or a combination of said snake venom with thrombotic activity and thrombin.

12. The reagent of claim 1, wherein said reagent is one member selected from the group consisting of streptokinase and urokinase.

13. The reagent of claim 1, wherein said reagent comprises one member selected from the group consisting of natural and synthetic tissue plasminogen activators.

14. The reagent of claim 1, wherein said reagent is an alpha-2-antiplasmin assay reagent containing fibrin and plasmin.

15. The reagent of claim 1, wherein said reagent comprises:
   (4) thrombin or a snake venom with thrombotic activity; and
   (8) one member selected from the group consisting of natural and synthetic plasminogen activators.

16. The reagent of claim 1, wherein said reagent comprises at least one member selected from the group consisting of streptokinase, tissue plasminogen activator and urokinase.

17. The reagent of claim 1, wherein said reagent is thrombomodulin or recombinant thrombomodulin.

18. The reagent of claim 1, wherein said one or more metals is at least one member selected from the group consisting of cerium, praseodymium, neodymium, promethium, samarium, europium, gadolinium, terbium, dysprosium, holmium, erbium, thulium, ytterbium, and lutetium.

19. The reagent of claim 18, wherein said reagent is thrombomodulin or recombinant thrombomodulin.

20. A reagent for performing a Protein C assay, comprising:
   an initiator of an intrinsic blood coagulation pathway or Factor X;
   a Protein C activator;
   calcium ions; and one or more lanthanide metal compounds that interact with calcium binding sites in a blood coagulation cascade.

21. The reagent of claim 20, wherein said Protein C activator is a thrombomodulin.

22. The reagent of claim 20, wherein said one or more metal compounds are one or more members selected from the group consisting of compounds of terbium, gadolinium, europium and lanthanum.

23. The reagent of claim 20, further comprising one or more bulkers, stabilizers or both.

* * * * *